United States Patent
Narula et al.

(10) Patent No.: US 8,859,820 B1
(45) Date of Patent: *Oct. 14, 2014

(54) 3-METHYL-6-CYCLOHEXADECEN-1-ONE AND ITS USE IN PERFUME COMPOSITIONS

(71) Applicant: International Flavors & Fragrances Inc., New York, NY (US)

(72) Inventors: Anubhav P. S. Narula, Hazlet, NJ (US); Edward Mark Arruda, Easton, PA (US); Benjamin Amorelli, Farmingdale, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/869,109

(22) Filed: Apr. 24, 2013

Related U.S. Application Data

(63) Continuation of application No. 13/214,315, filed on Aug. 22, 2011, now Pat. No. 8,450,265.

(51) Int. Cl.
*C07C 49/527* (2006.01)
*C11B 9/00* (2006.01)
*A61K 8/18* (2006.01)

(52) U.S. Cl.
CPC .................................... *C11B 9/0038* (2013.01)
USPC ............................................. 568/375; 512/27

(58) Field of Classification Search
CPC ......... C11B 9/0015; A61Q 13/00; A61K 8/35
USPC .............. 568/375; 512/27; 510/102
See application file for complete search history.

(56) References Cited

U.S. PATENT DOCUMENTS

| | | | | |
|---|---|---|---|---|
| 3,718,696 A | * | 2/1973 | Mookherjee et al. | 568/346 |
| 3,923,699 A | * | 12/1975 | Komatsu et al. | 512/2 |
| 3,935,270 A | * | 1/1976 | Calderon | 568/365 |
| 6,057,372 A | * | 5/2000 | Nobuhiro et al. | 514/675 |
| 6,200,254 B1 | * | 3/2001 | Lupo et al. | 512/8 |
| 6,326,349 B1 | * | 12/2001 | Helmlinger et al. | 512/26 |
| 7,129,380 B2 | * | 10/2006 | Reckziegel et al. | 568/375 |

* cited by examiner

*Primary Examiner* — Sikarl Witherspoon
(74) *Attorney, Agent, or Firm* — Elizabeth M. Quirk; XuFan Tseng; Joseph F. Leightner

(57) ABSTRACT

The present invention is directed to a novel fragrance compound, 3-methyl-cyclohexadec-6-enone.

1 Claim, No Drawings

3-METHYL-6-CYCLOHEXADECEN-1-ONE AND ITS USE IN PERFUME COMPOSITIONS

STATUS OF RELATED APPLICATIONS

This application is a continuation of U.S. Ser. No. 13/214,315, filed Aug. 22, 2011, now allowed, the contents hereby incorporated by reference as if set forth in its entirety.

FIELD OF THE INVENTION

The present invention relates to a new chemical entity and its use as a fragrance material.

BACKGROUND OF THE INVENTION

There is an ongoing need in the fragrance industry to provide new chemicals to give perfumers and other persons the ability to create new fragrances for perfumes, colognes and personal care products.

The odor of musk is a universally appreciated fragrance and is usually thought of as the animal note in perfumes. A number of naturally occurring species, both of animal and vegetable origin, possess musk odors; however, only the animal sources have achieved any commercial importance. It is because of the high demand, short supply, and expensive cost of these naturally occurring musk odorants that numerous attempts have been made, since the 1920's to synthesize compounds which would duplicate these desirable odors. It has been long and well known that macrocyclic carbonyl compounds having more than 13, but fewer than 19, carbon atoms are involved in achieving a musk odor (See, U.S. Pat. No. 6,326,349).

For example, Mookherjee, et al., U.S. Pat. No. 3,718,696, disclose the preparation of a mixture of Muscone (3-methyl-1-cyclopentadecanone, Formula I) and α-methyl-cyclopentadecanone (Formula II) (1973).

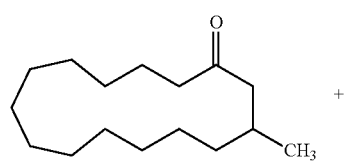

I

+

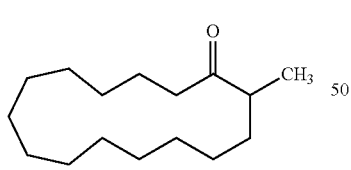

II

Komatsu, et al., U.S. Pat. No. 3,923,699, disclose Ambretone (or Velvione) (cyclohexadecenone-5, Formula III) (1975).

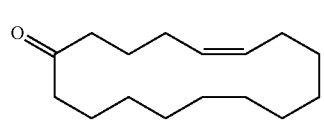

III

Calderon, U.S. Pat. No. 3,935,270, describes previously reported macrocyclic musk ketones including Civetone (9-cycloheptadecenone-1, Formula IV), Dihydrocivetone (cycloheptadecanone, Formula V), and Exaltone (cyclopentadecanone, Formula VI) (1976).

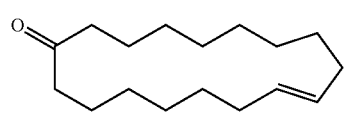

IV

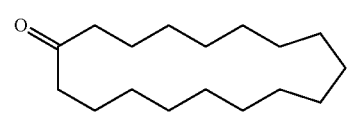

V

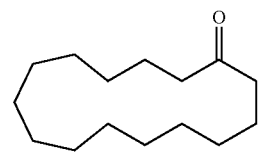

VI

More recently, Nobuhiro, et al., U.S. Pat. No. 6,057,372, disclose Animusk (or Globanone) (8-cyclohexadecen-1-one, Formula VII) (2000).

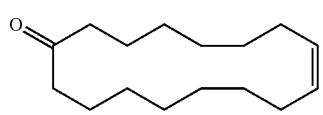

VII

Helmlinger, et al., U.S. Pat. No. 6,326,349, disclose Cosmone (3-methyl-cyclotetradec-5-en-1-one, Formula VIII) (2001).

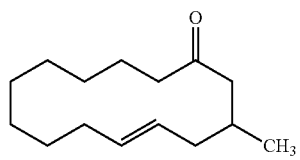

VIII

Reckziegel, et al., U.S. Pat. No. 7,129,380, disclose Aurelione (a mixture of 7-cyclohexadecen-1-one, Formula IX, and 8-cyclohexadecen-1-one, Formula VII) (2006).

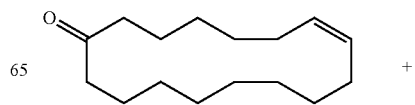

IX

+

-continued

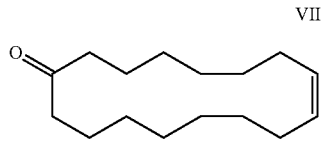
VII

Skilled in the art appreciate that small structural differences such as the number of double bonds and their positions in the ring would result in macrocyclic ketones with distinctive fragrance properties in addition to the musky odor. These distinctive properties can be highly valuable. They allow perfumers to create perfumes with unique and distinguished characters. However, many of these distinctive properties can also be undesirable and, thus, would render the macrocyclic ketones not suited for perfume use despite the musky odor. Further, practical considerations such as synthesis may also prevent the use of various macrocyclic ketones in commercial fragrance applications (See, U.S. Pat. No. 6,200,254).

It is well recognized by the art that whether a given macrocyclic ketone possesses useful fragrance properties and whether its synthesis can be carried out at a commercial scale are unpredictable. It requires undue experimentation to develop a particular macrocyclic ketone that meets the criteria of applicability based on the general knowledge in the art. For these reasons, a continuous and extensive effort has been made throughout the decades to search for novel macrocyclic ketone molecules suitable for fragrance use that can be produced via an economical process.

SUMMARY OF THE INVENTION

The present invention provides a novel compound and its unexpected advantageous use in enhancing, improving or modifying the fragrance of perfumes, colognes, toilet waters, fabric care products, personal products and the like.

More specifically, the present invention is directed to a novel compound, 3-methyl-cyclohexadec-6-enone, which exhibits unexpected strong and unique fragrance effect and a method of improving, enhancing or modifying a fragrance formulation through the addition of an olfactory acceptable amount of 3-methyl-cyclohexadec-6-enone:

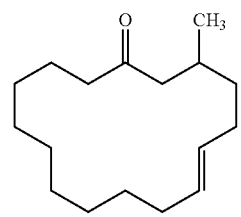
Formula X

3-Methyl-cyclohexadec-6-enone possesses a strong musky odor with an unexpected powdery character. Surprisingly, 3-methyl-cyclohexadec-6-enone also imparts unique and highly desirable properties in the top and middle notes such as feminine, smooth, creamy, warm, and comfortable characters.

These and other embodiments of the present invention will be apparent by reading the following specification.

DETAILED DESCRIPTION OF THE INVENTION

3-Methyl-cyclohexadec-6-enone of the present invention can be prepared from readily available starting material, 10-undecen-1-ol (commercially available at Sigma-Aldrich Inc.) in five steps with a ring closure Metathesis reaction. The reaction steps can be depicted by a scheme shown as follows:

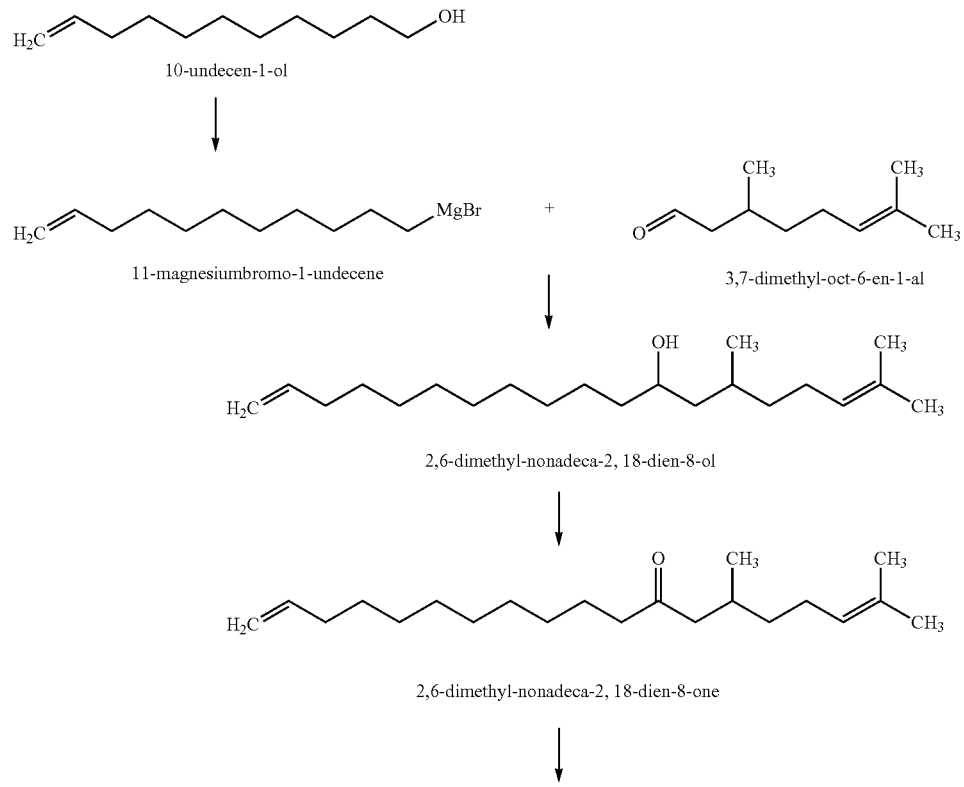

-continued

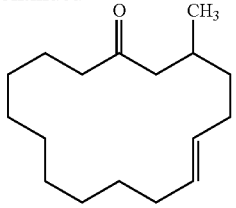

3-methyl-cyclohexadec-6-enone

Those with skill in the art will recognize that the compound of the present invention may have a number of isomers including optically active forms. It is intended herein that the compound described herein includes isomeric mixtures as well as specific enantiomers that may be separated using techniques known to those having skill in the art. Suitable techniques include chromatography such as high performance liquid chromatography, referred to as HPLC, and particularly gel chromatography and solid phase microextraction, referred to as SPME.

The compound of the present invention is surprisingly found to possess strong and unexpected fragrance effect such as, for example, woody, musky, powdery, feminine, creamy, warm, and comfortable notes.

The use of the compound of the present invention is widely applicable in current perfumery products, including the preparation of perfumes and colognes, the perfuming of personal care products such as soaps, shower gels, and hair care products, fabric care products as well as air fresheners and cosmetic preparations. The compound can also be used to perfume cleaning agents, such as, but not limited to detergents, dishwashing materials, scrubbing compositions, window cleaners and the like. In these preparations, the compound of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The term "improving" in the phrase "improving, enhancing or modifying a fragrance formulation" means raising the fragrance formulation to a more desirable character. The term "enhancing" means making the fragrance formulation greater in effectiveness or providing the fragrance formulation with an improved character. The term "modifying" means providing the fragrance formulation with a change in character.

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compound of the present invention employed in a fragrance formulation varies from about 0.005 to about 50 weight percent, preferably from 0.1 to about 25 weight percent, and more preferably from about 0.5 to about 10 weight percent. Those with skill in the art will be able to employ the desired amount to provide desired fragrance effect and intensity. In addition to the compound of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, the compound of the present invention provides unexpected strong woody, musky, powdery, feminine, creamy, warm, and comfortable characteristics and makes the fragrance formulation more desirable and noticeable. The odor qualities found in the compound of the present invention assist in beautifying and enhancing the finished accord and improve the performance of other materials in the fragrance formulation.

The following are provided as specific embodiments of the present invention. Other modifications of this invention will be readily apparent to those skilled in the art. Such modifications are understood to be within the scope of this invention. All reaction reagents were purchased from Sigma-Aldrich Inc. unless noted otherwise. As used herein all percentages are weight percent unless otherwise noted, ppm is understood to stand for parts per million, L is understood to be liter, mL is understood to be milliliter, mol is understood to be mole, mmol is understood to be millimole, Kg is understood to be kilogram, g is understood to be gram, and mmHg be millimeters (mm) of mercury (Hg). IFF as used in the examples is understood to mean International Flavors & Fragrances Inc., New York, N.Y., USA.

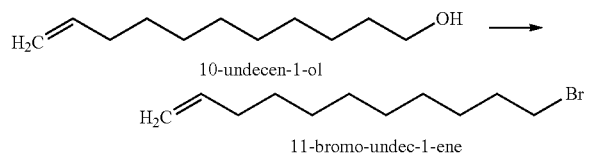

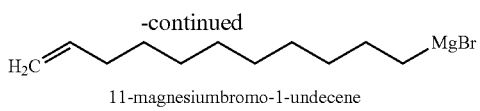

11-magnesiumbromo-1-undecene

Preparation of 11-magnesiumbromo-1-undecene

A two liter reaction flask was fitted with a mechanical stirring apparatus, a condenser, an addition funnel, a thermocouple, and a heating mantle. The reaction flask was flame dried, and then cooled under a nitrogen atmosphere to room temperature. Under a static nitrogen blanket the reaction flask was charged with magnesium turnings (29 g, 1.2 mol), tetrahydrofuran (THF, 1 L), and 1,2-dibromoethane (1 g) with stirring. The reaction flask was heated to 30-40° C., followed by the dropwise addition of 11-bromo-undec-1-ene (232 g, 1 mol, prepared as above in EXAMPLE I). The reaction mixture was subsequently aged for 4 hours and then allowed to cool to room temperature. The resulting mixture was directly used in the next step.

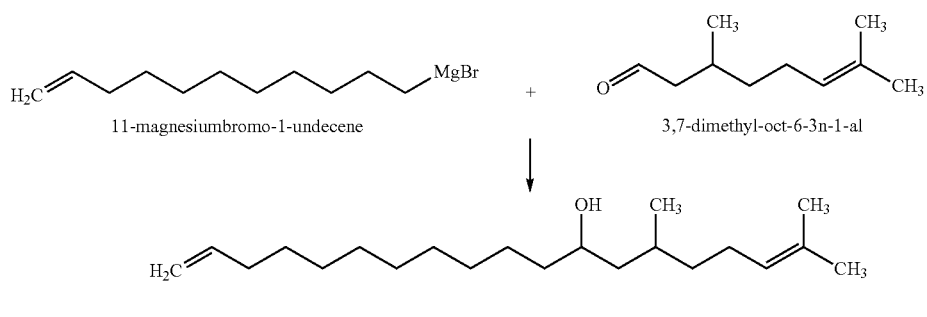

2,6-dimethyl-nonadeca-2,18-dien-8-ol

Preparation of 11-bromo-undec-1-ene

A five liter reaction flask was fitted with a mechanical stirring apparatus, a condenser, an addition funnel, and a thermocouple. The reaction flask was flame dried, and then cooled under a nitrogen atmosphere to room temperature. Under a static nitrogen blanket the reaction flask was charged with 10-undecen-1-ol (468 g, 3 mol) and toluene (1 L) while stirring. The contents were cooled to −10° C. and phosphorus tribromide (270 g, 1 mol) was added dropwise. The temperature was maintained at −10° C. with the aid of a Jack-o-matic, and the reaction mixture was aged for one hour. The reaction mixture was subsequently quenched and washed with brine (1 L). The organic layer was removed, and the product was distilled to provide 11-bromo-undec-1-ene (boiling point 95° C. at a pressure of 10 mm Hg).

$^1$H NMR: 5.77-5.86 ppm (m, 1H), 4.99 ppm (d, 1H, J=17.2 Hz), 4.93 ppm (d, 1H, J=10.2 Hz), 3.42 ppm (t, 2H, J=6.9 Hz), 2.01-2.07 ppm (m, 2H), 1.81-1.89 ppm (m, 2H), 1.36-1.43 ppm (m, 4H), 1.29 ppm (br, 8H)

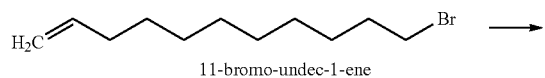

Preparation of 2,6-dimethyl-nonadeca-2,18-dien-8-ol 3,7-Dimethyl-octa-6-en-1-al (140 g, 1 mol) was added dropwise to 11-magnesiumbromo-1-undecene (prepared as above in EXAMPLE II). The reaction temperature was maintained at 30-40° C. Following the consumption of starting reactant 3,7-dimethyl-octa-6-en-1-al, the reaction was cooled to 0° C., quenched with acetic acid (15% aqueous solution, 500 mL), and extracted with toluene (500 mL). The organic layer was washed with sodium acetate (20% aqueous solution, 500 mL), and then brine (500 ml). The organic layer was concentrated under vacuum via rotary evaporator and then chromatographed on silica gel with ethyl acetate in hexanes (8%) as the eluent providing 2,6-dimethyl-nonadeca-2,18-dien-8-ol as a colorless oil.

$^1$H NMR: 5.81 ppm, (d, 1H, J=17.03 Hz, of d, J=10.22 Hz); 5.10 ppm, (t, 1H, J=5.63 Hz); 4.96 ppm, (d, 1H, J=16.09 Hz); 4.93 ppm, (d, 1H, J=10.17 Hz); 3.69 ppm (m, 1H); 1.95-2.06 ppm, (m, 4H); 1.68 ppm, (s, 3H); 1.60 ppm, (s, 3H); 1.56 ppm, (br. s, 1H); 1.14-1.49 ppm, (m, 21H); 0.91 ppm, (t, 3H, J=6.70 Hz).

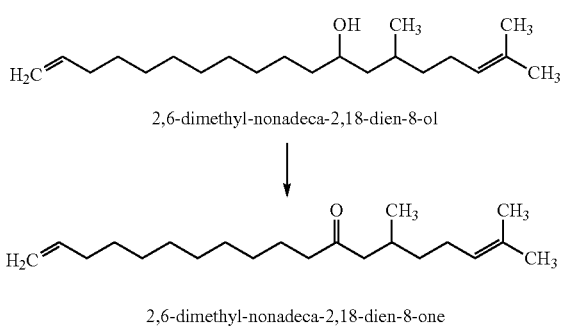

2,6-dimethyl-nonadeca-2,18-dien-8-ol

↓

2,6-dimethyl-nonadeca-2,18-dien-8-one

Preparation of
2,6-dimethyl-nonadeca-2,18-dien-8-one

Pyridinium chlorochromate (15 g, 0.07 mol) was added to a solution of 2,6-dimethyl-nonadeca-2,18-dien-8-ol (18 g, 0.058 mol, prepared as above in EXAMPLE III) in dichloromethane (100 mL) and stirred at room temperature for 6 hours. Silica gel (~15 g) was added to the reaction mixture, and the resulting mixture was concentrated via rotary evaporation. The crude concentrated mixture was scrapped away from the flask with a spatula and filtered through a silica gel plug using ethyl acetate (100%). The filtrate was concentrated and chromatographed on silica gel with ethyl acetate in hexanes (2%) as the eluent providing 2,6-dimethyl-nonadeca-2, 18-dien-8-one as a colorless oil (15 g).

$^1$H NMR: 5.77-5.83 ppm, (m, 1H); 5.08 ppm, (s, 1H); 4.98 ppm, (d, 1H, J=17.09 Hz); 4.92 ppm, (d, 1H, J=10.05 Hz); 2.34-2.40 ppm, (m, 2H); 2.17-2.22 ppm, (m, 1H); 1.92-2.06 ppm, (m, 5H); 1.68 ppm, (s, 3H); 1.59 ppm, (s, 3H); 1.51-1.57 ppm, (m, 2H); 1.15-1.41 ppm, (m, 15H); 0.89 ppm, (d, 3H, J=6.48 Hz).

The compound 2,6-dimethyl-nonadeca-2,18-dien-8-one was described as having aldehydic, musky, woody, floral, fruity, minty, and clean notes.

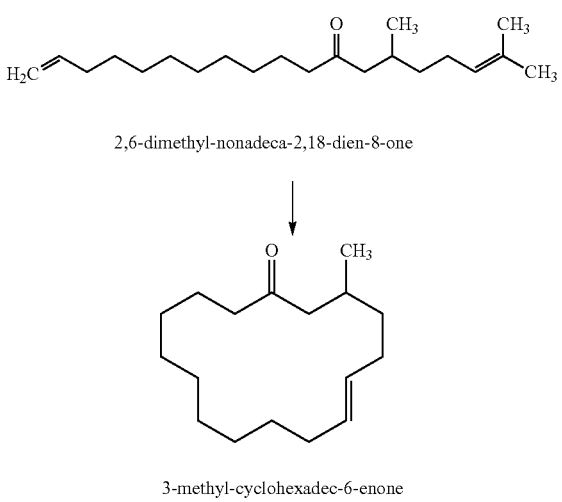

2,6-dimethyl-nonadeca-2,18-dien-8-one

↓

3-methyl-cyclohexadec-6-enone

Preparation of 3-methyl-cyclohexadec-6-enone
(Formula X)

Grubbs' Catalyst, 2$^{nd}$ generation (benzylidene [1,3-bis(2, 4,6-trimethylphenyl)-2-imidazolidinylidene] dichloro (tricyclohexylphosphine) ruthenium) (560 mg, 0.066 mmol, 2 mol %), was added to a solution of 2,6-dimethyl-nonadeca-2,18-dien-8-one (1 g, 3.3 mmol, prepared as above in EXAMPLE IV) in dichloromethane at room temperature. The reaction mixture was stirred at reflux for 12 hours. The reaction mixtures was subsequently concentrated and then chromatographed on silica with ethyl acetate in hexanes (2%) as the eluent providing 3-methyl-cyclohexadec-6-enone as a colorless oil (0.4 g). This oil was then filtered through a slurry of silica gel/activated charcoal.

$^1$H NMR: 5.35 ppm, (t, 1H, J=6.06 Hz); 2.30-2.52 ppm, (m, 3H); 1.97-2.23 ppm, (m, 6H); 1.66-1.73 ppm, (m, 1H); 1.52-1.62 ppm, (m, 1H); 1.16-1.44 ppm, (m, 14H), 0.95 ppm, (d, 28% of 3H, J=6.67 Hz); 0.90 ppm, (d, 72% of 3H, J=6.53 Hz).

The compound 3-methyl-cyclohexadec-6-enone was described as having woody, musky, powdery, feminine, creamy, warm, and comfortable notes.

| Ingredients | Parts |
| --- | --- |
| Allyl amyl glycolate | 1.00 |
| Benzyl acetate | 10.00 |
| Benzyl salicylate | 55.00 |
| Bergamot oil | 35.00 |
| Cashmeran | 4.00 |
| Cedrenyl acetate | 20.00 |
| Citronellol | 50.00 |
| Coumarin | 25.00 |
| Cyclogalbaniff | 3.00 |
| 3-Methyl-cyclohexadec-6-enone | 7.50 |
| Damascone, delta | 0.40 |
| Ethyl vanillin | 1.00 |
| Eugenol | 40.00 |
| Galaxolide | 90.00 |
| Galbanum oil ref a lmr | 0.10 |
| Geraniol | 13.00 |
| Hedione | 80.00 |
| Helional | 6.00 |
| Heliotropine | 20.00 |
| Hexenyl salicylate, cis-3 | 13.00 |
| Ionone beta | 10.00 |
| Iso e super | 60.00 |
| Jasmin abs egypt lmr | 5.00 |
| Lilial | 40.00 |
| Linalool | 80.00 |
| Linalyl acetate | 65.00 |
| Lyral | 40.00 |
| Methyl anthranilate | 8.00 |
| Methyl ionone gamma | 55.00 |
| Muskalactone | 25.00 |
| Olibanum coeur dep 50 pct | 6.00 |
| Patchouli oil | 35.00 |
| Sandalore | 20.00 |
| Sanjinol | 20.00 |
| Styralyl acetate | 10.00 |
| Vanillin | 13.00 |
| Veramoss | 4.00 |
| Vertofix | 25.00 |
| Ylang oil | 5.00 |
| Total | 1000.00 |

The above fragrance has musk, powdery, feminine, creamy, warm, and comfortable tones.

| Compounds | Odor Profiles |
| --- | --- |
| 3-Methyl-cyclohexadec-6-enone (Formula X) | Strong, musk, powdery, feminine, smooth, creamy, warm, comfortable |
| 9-Cycloheptadecenone-1 (Formula IV) | Animal, civet, fecal |
| Cycloheptadecanone (Formula V) | Animal, less fecal |
| Cyclopentadecanone (Formula VI) | Strong, musk, sweet, animal |

-continued

| Compounds | Odor Profiles |
|---|---|
| 8-cyclohexadecen-1-one (Formula VII) | Weak to medium, musk, sweet, slightly woody |

The above evaluation demonstrated that 3-methyl-cyclohexadec-6-enone (Formula X) displayed a strong musky odor with an unexpected powdery character. 3-Methyl-cyclohexadec-6-enone also imparted unique properties in the top and middle notes such as feminine, smooth, creamy, warm, and comfortable characters. Thus, a double bond in the 6-position and a methyl group in the 3-position of a 16-membered macrocyclic ketone unexpectedly provide a superior odor profile and facets to the musk odor.

What is claimed is:
1. A compound, 3-methyl-cyclohexadec-6-enone.

* * * * *